US006599515B1

(12) United States Patent
Delmotte

(10) Patent No.: US 6,599,515 B1
(45) Date of Patent: Jul. 29, 2003

(54) FIBRIN POROUS STRUCTURE

(75) Inventor: Yves Delmotte, Tertre (BE)

(73) Assignee: Baxter International Inc., Deerfield, IL (US)

( * ) Notice: Subject to any disclaimer, the term of this patent is extended or adjusted under 35 U.S.C. 154(b) by 0 days.

(21) Appl. No.: 09/566,372

(22) Filed: May 8, 2000

Related U.S. Application Data

(63) Continuation-in-part of application No. 08/679,658, filed on Jul. 12, 1996, now Pat. No. 5,989,215, which is a continuation-in-part of application No. PCT/EP96/00160, filed on Jan. 16, 1996.

(30) Foreign Application Priority Data

Jan. 16, 1995 (DE) .......................... 195 01 067

(51) Int. Cl.$^7$ ............................ A61M 37/00; A61F 2/00
(52) U.S. Cl. ...................... 424/422; 424/443; 424/423; 424/424; 424/426
(58) Field of Search ................................ 424/422, 443, 424/423, 424, 426

(56) References Cited

U.S. PATENT DOCUMENTS 4,442,655 A * 4/1984 Stroetmann ............... 53/428
5,206,140 A * 4/1993 Marder et al. ............... 435/7.1
5,288,490 A * 2/1994 Budzynski et al. ...... 424/94.64
5,318,524 A 6/1994 Morse et al.
5,989,215 A 11/1999 Delmotte et al.
6,074,663 A * 6/2000 Delmotte et al. ........... 424/443

FOREIGN PATENT DOCUMENTS

| WO | WO 96/22115 | 7/1996 |
|---|---|---|
| WO | WO 98/02098 | 1/1998 |
| WO | WO 99/29338 | 6/1999 |
| WO | WO 01/54735 | 8/2001 |

* cited by examiner

Primary Examiner—Thurman K. Page
Assistant Examiner—Rachel M. Bennett
(74) Attorney, Agent, or Firm—Bell, Boyd & Lloyd LLC

(57) ABSTRACT

The present invention provides a porous structure of fibrin or fibrinogen material. The structure in its substantially dry form, having a compression strain of less than 8%, and a creep modulus higher than $1.5 \times 10^6$ Pa. The compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute. After hydration, the structure has a porosity wherein at least 50% by volume of the total porosity is formed by channels with an open cross section of more than 500 $\mu m^2$.

33 Claims, 9 Drawing Sheets

LYOPHILYSED FIBRIN (PBS)

before hydration

LYOPHILYSED FIBRIN (PBS)
after hydration

LYOPHILYSED FIBRIN (PBS)
before hydration

LYOPHILYSED FIBRIN (PBS)
after hydration

Fibrin: Tisseel 1:2 / Thrombin 20IU

Freeze Dried

Hydrated (H2O)

Fibrin: Tisseel 1:2 / Thrombin 20IU

Freeze Dried

Hydrated (H2O)

Fibrin: Tisseel 1:2 / Thrombin 20IU

Fibrin: Tisseel 1:2 / Thrombin 20IU

FIBRIN POROUS STRUCTURE

RELATED APPLICATIONS

This is a continuation-in-part application of U.S. application Ser. No. 08/679,658, filed on Jul. 12, 1996, now U.S. Pat. No. 5,989,215, which is a C-I-P of PCT/EP96/00160, filed Jan. 16, 1996, which is incorporated herein by reference and made a part hereof.

TECHNICAL FIELD

This invention provides a fibrin porous structure material and particularly a fibrin porous structure having good resistance to compression and a porosity formed by large cells.

BACKGROUND ART

Fibrin sponges are known from U.S. Pat. No. 4,442,655 and WO99/15209. The fibrin sponges have a porous structure and have substantially no compression strength. After hydration, the sponges have cells having a cross section area of less than about 100 $\mu m^2$, i.e., a porosity which is different from the porosity of a natural human bone.

As explained in the '655 patent, the sponge structure is obtained by freeze-drying a reaction mixture containing fibrinogen, fibrin and a catalytic amount of thrombin. None of the examples of the '655 patent relates to the freeze-drying of a solution containing fibrin partially cross-linked due to the presence of an anticoagulant increasing the clotting time.

It has now been found that, after lyophilizing a solution containing fibrin partially cross-linked due to the presence of a sufficient amount of a calcium inhibiting or blocking agent, preferably an anticoagulant, it was possible to obtain a solid porous structure having an open cross section of more than 500 $\mu m^2$ and/or a wall thickness between channels of at least 10 $\mu m$. Those skilled in the art were unable to predict that it would be able to prepare fibrin porous structure having a good resistance to compression and a porosity formed by large cells, such as in the natural human bone.

BRIEF DESCRIPTION OF THE INVENTION

The invention relates to a porous structure comprising fibrin or fibrinogen material, and possibly other compounds, the structure having:

in its substantially dry form, a compression strain of less than about 8%, preferably less than about 7%, and most preferably from about 6 and to about 7%, and a creep modulus higher than $1.5 \times 10^6$ Pa, advantageously higher than $1.7 \times 10^6$ Pa, most preferably from about $1.8 \times 10^6$ Pa to about $2.5 \times 10^6$ Pa, said compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute, and after hydration, such a porosity that at least about 50% by volume of the total porosity is formed by channels with an open cross section of more than 500 $\mu m^2$.

These large pores are suitable for the attachment of cells on the structure. Moreover, according to an embodiment, such large pores are similar to the pores of human natural bones.

Advantageously, the mechanical properties of the porous structure of the invention are kept after successive compression steps, separated the one from another by a release step.

Advantageously, the structure, in its substantially dry form, has a compression strain of less than about 8%, more preferably less than about 7%, most preferably from about 6% to about 7%, and a creep modulus higher than $1.5 \times 10^6$ Pa, advantageously higher than $1.7 \times 10^6$ Pa, for example between about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after ten cycles consisting of a compression step of 2500 milli Newtons with a compression ramp of 500 milli Newtons per minute followed by a compression release step.

It has also been observed that it was interesting to adjust the atomic ratio of calcium and phosphorus (Ca/P) of the structure, preferably between 1 and 2, most preferably between 1.67 and 1.95, for the formation of hydroxyapatite.

The structure of the invention can be used, after grinding, as a powder. Such a powder can, for example, be added to a liquid or to form a liquid glue.

The structure of the invention that has a good compression resistance and larger pores can be used as support for a skin layer and/or for a sponge structure, especially a fibrin sponge structure.

A titanium support can also be provided with a layer of the porous structure of the invention, or with a layer of a powder of the porous structure of the invention, or with a layer containing a powder of the structure of the invention. Preparation processes of such titanium supports will be disclosed after the description of processes of preparation of the structure of the invention.

The present invention further provides a process for preparing a porous structure of the invention. The process provides the steps of (1) providing a solution containing fibrin or fibrinogen materials (advantageously at least 3 mg/ml), (2) polymerizing the fibrin or fibrinogen, preferably a polymerization with at least partial cross-linking of the fibrin or fibrinogen materials in the presence of a calcium blocking or inhibiting agent (preferably an anticoagulant), and (3) lyophilizing the polymerized fibrin or fibrinogen. The calcium blocking or inhibiting agent should be present in the solution in an amount sufficient for preparing a porous structure. The resulting fibrin or fibrinogen material should have:

in its substantially dry form, a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute, and after hydration, such a porosity that at least 50% by volume of the total porosity is formed by channels with an open cross section of more than about 500 $\mu m^2$.

Calcium inhibiting agent means an agent suitable for inhibiting at least partly the functionality of one or more calcium sites of the fibrin or fibrinogen material. The calcium inhibiting agent is preferably a calcium blocking agent, most preferably an anticoagulant.

DETAILED DESCRIPTION OF THE INVENTION

The present invention relates to a porous structure comprising fibrin or fibrinogen material, and possibly other compounds, the structure having:

in its substantially dry form, a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute, and after hydration, such a porosity that at least 50% by volume of the total porosity is formed by channels with an open cross section of more than about 500 $\mu m^2$.

In the present specification, the wordings "substantially dry form" mean a residual moisture level of less than about 1%, and more preferably of less than about 0.5%.

The structure of the invention has advantageously a low moisture content, for example a moisture content of less than about 7.5%, preferably of less than about 2%, most preferably of less than about 1%, and more specifically less than about 0.5%. In the event the moisture content of the structure of the invention is greater than 1%, for the determination of the mechanical properties of the structure of the invention in its substantially dry form, the moisture content has to be lowered to less than about 1%, by using a technique not degrading the bounds of the structure.

In a preferred form of the invention, the mechanical properties of the porous structure of the invention are retained after successive steps of compressing the structure with release steps between the compressing steps. Advantageously, the structure, in its substantially dry form, has a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after ten cycles consisting of a compression step of 2500 milli Newtons with a compression ramp of 500 milli Newtons per minute followed by a compression release step.

Preferably, the mechanical properties of the porous structure of the invention are at least retained in part after rehydration. Advantageously, the structure, in its hydrated form, has a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after one cycle, preferably after ten cycles, consisting each of a compression step of 2500 milli Newtons with a compression ramp of 500 milli Newtons per minute followed by a compression release step.

Advantageously, the structure has fibrin or fibrinogen dimensions such that, after hydration, the ratio of the volume of hydrated structure versus the volume of the dry structure is from about 0.5 to about 1.5, more preferably from about 0.7 to about 1.2, and most preferably from about 0.9 to about 1.1.

According to a preferred embodiment, the structure comprises walls defining therebetween cells, at least part of said cells are linked so as to define channels having after hydration in cross section an open section greater than about 500 $\mu m^2$, more preferably greater than about 1000 $\mu m^2$, and most preferably from about 3,000 $\mu m^2$ to about 300,000 $\mu m^2$. Preferably, at least 50% of the total porosity of the structure is formed by channels with an open cross section of more than about 1000 $\mu m^2$. According to a detail of a specific embodiment, the channels of the structure are homogeneously dispersed and have a substantially identical open cross-section. For example, 80% of the total porosity is formed by channels with an open cross-section from about 0.75 to about 2 times the mean open cross section of said channels. In order to determine the open cross section of the channels of the structure, the structure is cut perpendicular or substantially perpendicular to the axis of the channels, said cut being thereafter visualized by means of a microscope, electronic microscope, or any appropriate techniques.

According to an embodiment, the structure has an apparent density calculated in its substantially dry form of less than about 0.5 $g/cm^3$, advantageously less than about 0.3 $g/cm^3$, for example between 0.05 and 0.2 $g/cm^3$. Apparent density corresponds to the weight of a cube of 1 $cm^3$ of the porous structure. When the channels of the porous structure are filled with water by immersing the structure into a bath, the structure falls towards the bottom of the bath. By determining the volume of the walls of the structure (volume increase of the bath when immersing a cube of 1 $cm^3$ of the porous structure in the bath) and by determining the weight of the cube, it is possible to determine the density of the walls of the structure.

The walls have advantageously an average thickness of less than about 100 $\mu m$, advantageously from about 10 to about 80 $\mu m$, preferably from about 20 to about 60 $\mu m$. The thickness is for example measured by scanning electron microscope (SEM—Philips XL20)

As the channels of the structure have a high open cross section, the surface area of the structure is low. For example, the surface area of the structure is less than about 1 $m^2/g$, especially less than about 0.5 $m^2/g$.

Preferably, the atomic ratio Ca/P of the structure is adjusted. For example, the atomic ratio is from about 0.5 to about 5, preferably lower than about 2, most preferably from about 1.67 to about 1.95.

According to an embodiment, the structure contains calcium which is substantially not bound to albumin and/or to fibrin and/or to fibrinogen materials, and/or the structure has a low albumin content, for example the weight ratio fibrin/albumin of the solution used for the preparation of the structure is greater than about 2, advantageously greater than about 4, most preferably greater than about 8.

The structure has, for example, a ratio of the volume of the porous structure in its substantially dry form to the volume of the structure in its hydrated form (i.e. hydrated after the lyophilization step) is from about 0.7 to about 1.7, advantageously from about 0.8 to about 1.2, and most preferably about 1.

The structure can be sterilized, by treatment with sterilizing agent, by gamma radiation, by X rays, with ethylene oxide, etc. The treatment is preferably a treatment that does not denature the fibrin. Sterilization of the structure is preferably below −25° C., and most preferably below −80° C. at a dosage of at least 25 kGy.

The structure of the present invention is substantially pyrogen free.

The structure of the present invention which is provided with cells or channels, comprises at least a binding agent, for example in the form of a layer, on at least a part of the surface of cells.

The structure of the present invention can also include an additive (for example within the wall of the channels or cells of the structure) or is provided with a layer containing at least an additive, said additive being selected from the group consisting of processing aids (such as lubricant, plastifying agent, surfactant, viscosity reducing agent, etc.), fibers, polymers, copolymers, antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferon's, hormones, polysaccharides, genetic materials, proteins promoting or stimulating the growth and/or attachment of endothelial cells on the cross-linked fibrin, growth factors,.cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_{12}$–$C_{24}$ fatty acids, etc. and mixtures thereof.

The term "genetic material" as used herein refers to nucleotide based materials, including without limitation, viruses and viral fragments, deoxyribonucleic acid (DNA), plasmids, ribonucleic acid (RNA), messenger RNA (mRNA), transfer RNA (tRNA), ribosomal RNA (rRNA), catalytic RNA (cRNA), smaller nuclear RNA (snRNA), exons, introns, codons, and anti-sense oligonucleotides. Genetic material, especially viruses and viral fragments, may incidentally include some protein. In addition, the term "recombinant material" as used herein refers to material manufactured by recombinant technology which is a series of procedures that are used to join (recombine) segments of two or more different DNA molecules. A recombinant DNA molecule can enter a cell and replicate there, autonomously, or after it has become integrated into a chromosome.

The structure of the present invention comprises, according to a preferred embodiment, bone chips, such as bone chips or particles having an average particle size (average by weight) lower than 2 mm, for example from about 100 m to about 1 mm, advantageously from about 250 $\mu$m to about 750 $\mu$m, and most preferably about 500 $\mu$m.

The structure of the present invention contains for example from 1 to 85% by weight a bone chips, advantageously from 5 to 60%, preferably from 10 to 50%, most preferably from 15 to 30% by weight bone chips.

Another object of the invention is a powder of the structure of the invention. Such a powder can be prepared by milling or grinding a structure of the invention. The grain size of the powder is for example lower than 5 mm, advantageously from about 500 $\mu$m to about 2 mm. The grain size is however preferably lower than 1 mm.

Such a powder is possibly mixed with other solid particles, advantageously with bone chips, such as bone chips or particles having an average particle size (average by weight) lower than 2 mm, for example from about 100 $\mu$m to 1 mm, advantageously from about 250 $\mu$m to 750 $\mu$m, preferably about 500 $\mu$m.

Such a powder, advantageously mixed with bone particles, is suitable for preparing a glue or cement, for example for filling a hole in a bone. Advantageously, the glue is in a substantially liquid form or in the form of a paste, so that its application is easy. The powder of the invention, which possibly contains other additive(s), is thus used in the glue as filler. The glue or cement used can be any suitable and compatible glue or cement, said glue or cement possibly containing additive(s), active agent(s), etc.

A further object of the invention is a product consisting of powder of the invention which have been pressed together, possibly in presence of an additive, such as a binding agent, a lubricant, a plastizer, etc. and/or in presence of bone chips. The product has a higher density, is compact and the pores have a reduced pore size, for example an average pore size of less than 50 $\mu$m, advantageously less than 20 $\mu$m, preferably less than 10 $\mu$m. The product is characterized by a high volume increase when hydrated.

Still a further product of the invention consists of a laminated product comprising at least a layer having the structure of the invention. For example, the product comprises several layers having a structure of the invention or a layer with the structure of the invention forming an intermediate layer extending between two layers. The laminated product can possibly be compacted. The laminated product is dense, compact and has a high resistance to compression.

A further object of the invention is a bone substitute made of a structure according to the invention. The bone substitute can be manufactured for example by mechanically working a block having a structure according to the invention, by filling a mold with a glue or cement containing particles or powders having a structure of the invention. Advantageously, the bone substitute is made of a product having a structure of the invention, the volume of which remains substantially constant when hydrated. Preferably, the bone substitute is characterized in that the difference between the volume of the bone substitute in its substantially dry form and the volume of the bone substitute in its hydrated form is less than +/−5% of the volume.

Still a further object of the invention is a multilayer structure, said multi-layer structure comprising at least a structure of the invention. The multi-layer structure of the invention can for example comprise a first layer having a structure according to the invention, and a second layer selected from the group consisting of a structure according to the invention which is different from the first layer, a skin layer, a porous layer, a sponge layer, preferably the second layer is also a fibrin or fibrinogen layer.

The present invention relates also to a process for the preparation of a structure according to the invention. In said process, a solution containing fibrin or fibrinogen materials is polymerized, advantageously a polymerization with a at least partial cross-linking, of the fibrin or fibrinogen materials in presence of a calcium blocking or inhibiting agent (i.e. an agent inhibiting, advantageously blocking, the functionality of the calcium on one or more sites of the fibrin or fibrinogen material), and the solution of partially cross-linked fibrin or fibrinogen is lyophilized, whereby the calcium inhibiting or blocking agent is present in an amount sufficient for obtaining after the lyophilization a porous structure. The results structure having:
  in its substantially dry form, a compression strain of less
    than about 8%, preferably less than about 7%, and more
    preferably from about 6% to about 7%, and a creep
    modulus higher than 1.5×10⁶ Pa, more preferably
    higher than 1.7×10⁶ Pa, most preferably from about
    1.8×10⁶ Pa to about 2.5×10⁶ Pa, the compression strain
    and creep modulus being measured for a sample having
    a diameter of 5 mm on which a compression of 2500
    Milli Newtons is exerted with a compression ramp of 500 Milli Newtons per minute, after a compression release step following an initial compression of 2500 Milli Newtons with a compression ramp of 500 Milli Newtons per minute, and after hydration, such a porosity that at least 50% by volume of the total porosity is formed by channels with an open cross section of more than about 500 $\mu m^2$.

Advantageously, the calcium inhibiting or blocking agent is present in an amount sufficient for obtaining, after the lyophilization, a porous structure having mechanical properties which are substantially kept after successive compression steps, separated the one from another by a release step. Advantageously, the structure, in its substantially dry form, prepared by the process of the invention has a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after ten cycles consisting of a compression step of 2500 milli Newtons with a compression ramp of 500 milli Newtons per minute followed by a compression release step.

Preferably, the calcium inhibiting or blocking agent is present in an amount sufficient for obtaining after the lyophilization a porous structure having mechanical properties which are substantially kept after rehydration. Advantageously, the structure prepared by a preferred process of the invention has, in its hydrated form, a compression strain of less than about 8%, preferably less than about 7%, and more preferably from about 6% to about 7%, and a creep modulus higher than $1.5 \times 10^6$ Pa, more preferably higher than $1.7 \times 10^6$ Pa, most preferably from about $1.8 \times 10^6$ Pa to about $2.5 \times 10^6$ Pa, the compression strain and creep modulus being measured for a sample having a diameter of 5 mm on which a compression of 2500 milli Newtons is exerted with a compression ramp of 500 milli Newtons per minute, after one cycle, preferably after ten cycles, consisting each of a compression step of 2500 milli Newtons with a compression ramp of 500 milli Newtons per minute followed by a compression release step.

Advantageously, the polymerization, with an at least partial cross-linking, of the fibrin or fibrinogen materials is carried out in presence of an amount of calcium inhibiting or blocking agent sufficient for inhibiting or reducing the cross-linking rate so as to obtain after lyophilization walls defining therebetween channels, said channels having after rehydration in cross section an open section greater than about 1000 $\mu m^2$, and most preferably from about 3,000 $\mu m^2$ to about 300,000 $\mu m^2$.

Advantageously, the polymerization, with an at least partial cross-linking, of the fibrin or fibrinogen materials is carried out in presence of an amount of calcium inhibiting agent, preferably a calcium blocking agent, most preferably an anticoagulant, that is sufficient for obtaining after lyophilization a wall thickness of less than 30 $\mu m$, preferably of 5 to 15 $\mu m$.

According to an embodiment, the calcium inhibiting or blocking agent is selected from the group consisting of: citrate salts, phosphate salts, oxalate salts and mixtures thereof. Other possible calcium blocking agents are compounds blocking calcium sites of the fibrinogen, such as sodium polyphosphate, zeolithe, phosphate, potassium citrate, salt of phosphonic acid, amine, glycol, diethyleneglycol, triethanolamine, ammonium, betaine, glycerophosphate, aluminosilicate (zeolithe P), hexametaphosphate, polyacrylate, oligomeric phosphates, polyethyleneglycol, tannic acid, verapamil salt, piperidine dion derivatives, guanidine derivatives, amlodipine benzenesulfonate, 3-methylflavone-8-carboxylic acid esters, compounds having antagonist properties towards calcium ion, lidoflazine, etc., anticoagulants such as dextran, 2,6 dimethyl 4(2nitrophenyl) 1,4 dihydro pyridine 3,5 dimethyl dicarboxylate (Nifedipine), heparin, ((diphenylacetyl-4,5 oxazolyl-2)immino)-2,2' diethanol, trombarin, bisobrine, morphine, amphetamine, antibiotics having anti coagulant properties, sodium salt of the 4 amino 2 hydroxybenzoic acid, sodium citrate and mixtures thereof.

Preferably, the calcium blocking agent is also an anticoagulant such as dextran, 2,6 dimethyl 4(2nitrophenyl) 1,4 dihydro pyridine 3,5 dimethyl dicarboxylate (Nifedipine), heparin, ((diphenylacetyl-4,5 oxazolyl-2)immino)-2,2'diethanol, trombarin, bisobrine, morphine, amphetamine, antibiotics having anti coagulant properties, sodium salt of the 4 amino 2 hydroxybenzoic acid, sodium citrate and mixtures thereof.

The partial or complete polymerization, advantageously with a partial cross-linking, of the fibrin or fibrinogen is advantageously carried out at a pH from about 6 to about 10, more preferably from about 7 to about 8, most specifically at about 7.5. In order to ensure a substantially constant pH during the cross-linking, one or more buffers can be used. Preferably, the buffer has also a calcium inhibiting action.

Possibly, the partial or complete polymerization, advantageously with a partial cross-linking, is carried out at a pH lower than 6, but preferably at a pH sufficient for avoiding the denaturation of the fibrin or fibrinogen material. For example, the polymerization is carried out at least partly at a pH of from 4 to about 6, and preferably from about 5 to about 5.5. In this case, the calcium inhibiting or blocking agent is an acid, advantageously an organic acid, for example organic acid with 1 to 24 carbon atoms, most specifically citric acid, acetic acid, formic acid, tannic acid, etc., citric acid being preferred.

According to a possible embodiment, the polymerization is carried out in a first step at a first pH lower than about 6.5, and in a second step at a second pH higher than the first pH. For example, in the second step, the polymerization is carried out at a pH from about 6 to about 10, advantageously from about 6.5 to about 8, preferably at a pH from about 7 to about 7.5, and most specifically at a pH of from about 7.1 to about 7.4.

The polymerization, with, preferably, partial cross-linking, is carried out for example at a temperature from about 0° C. to about 60° C., advantageously at a temperature from about 5° C. to about 50° C., preferably at a temperature from about 20° C. to about 40° C., most preferably at a temperature of about 37° C. The polymerization can possibly be carried out at various temperatures. For example, in a first step the polymerization is carried out at a first temperature, while in a second step, the polymerization is carried out at a temperature higher than the first temperature. For example, in the first step, the temperature of the reaction medium is lower than about 30° C., preferably lower than about 25° C., for example from about 15° C. to about 25° C., while in the second step, the temperature of the reaction medium is higher than 30° C., for example from about 35° C. to about 50° C., most preferably about 37° C. Possibly, the temperature of the reaction medium is increased during the reaction, for example according to a substantially continuous path. For example, the reaction starts at a temperature lower than or about 20° C., and is progressively carried out at a temperature higher than 20° C., for example at an end temperature of about 37° C.

The fibrin or fibrinogen material after polymerization with partial cross-linking has advantageously, before its lyophilization, an osmolarity greater than about 175 mosm, preferably greater than about 200 mosm, most preferably greater than about 250 mosm, for example from about 250 to about 400 mosm. The fibrin or fibrinogen material after cross-linking has advantageously, before its lyophilization, has also advantageously an optical density lower than about 1 Absorbance Unit Full Scale, advantageously lower than about 0.5 AUFS. The osmolarity has been measured by measured by using the apparatus FISKE 2400 OSMOMETER (Fiske Associates) according to the following method:

A sample is supercooled several degrees below the freezing point. The heat of fusion liberated allows sample temperature to rise to a temporary "liquid-solid" equilibrium. The equilibrium is by definition the freezing point of the solution. The freezing point is related to stols to allow determination of osmolarity. The osmolarity is equal to the osmoles of solute per Kg of pure solvent.

The optical density has been measured at a wavelength of 800 nm (Absorbance Unit Full Scale).

According to a detail of a process of the invention, the polymerization, advantageously with an at least partial cross-linking of the fibrin or fibrinogen materials is carried out in presence of an effective amount of calcium inhibiting or blocking agent, preferably an anticoagulant, sufficient for having a clotting time of more than 30 seconds, advantageously of more than 60 seconds, most preferably of more than 200 seconds, said clotting time being measured in the apparatus "BFT II" of DADE BEHRING (Germany) at 37° C. This apparatus operates according to the opto-mechanical measuring principle (measure of a turbidity). A light beam passes through a plastic cuvette containing 0.5 ml of the solution to be analysed, onto a photodetector. The change of intensity of the transmitted light is converted into an electric signal. A stir bar is placed in the cuvette or cup so as to ensure homogeneity of the solution placed in the cuvette or cup.

The amount of calcium inhibiting or blocking agent can be determined by an individual skilled in the art by successive tests for adding different amounts of calcium or blocking agent.

Advantageously, the lyophilization step is carried out at a temperature of less than 40° C. and at a pressure of less than $0.4 \times 10^5$ Pa. For the lyophilization, it can be worthwhile to add some specific additive(s), such as glycerol, fatty acid, etc.

The lyophilization is advantageously carried out at different temperatures below about −10° C. For example, the lyophilization is first carried out at a temperature below than −40° C., and then at a temperature from about −40° C. to about −10° C. According to a possible embodiment, the lyophilization is carried out at a temperature varying substantially continuously from a temperature below −40° C. up to a temperature comprised between −40° C. and −10° C.

For example, the lyophilization is carried out in several steps, such as lowering the temperature to about −58° C. and maintaining said temperature during a period of time (for example from 1 to 30 hours, advantageously from 1 to 15 hours) while creating a vacuum, then increasing the temperature from −58° C. to −20° C. or −30° C. while maintaining the vacuum, then by maintaining the temperature of −20° C. or −30° C. while maintaining the vacuum (for example from 5 to 100 hours), then increasing the temperature to more than 20° C., while maintaining the vacuum.

During the lyophilization, it is possible to adjust the temperature and/or the pressure for obtaining a substantially constant pore distribution through the thickness of the fibrin-fibrinogen layer. For example, the vacuum is lowered when the temperature is increased, i.e., the pressure is increased when the temperature is increased.

The lyophilization can also be controlled so as to adjust the residual moisture of the porous structure of the invention at the end of the lyophilization step. Advantageously, the residual moisture of the porous structure at the end of the lyophilization step is lower than about 7.5%, advantageously lower than about 2%, preferably lower than about 1%, most preferably lower than about 0.5%.

The end moisture of the porous structure of the invention, after the lyophilization step, can possibly be adjusted by a subsequent drying step.

According to an embodiment, in the process of the invention, at least a phosphate salt is added in an amount sufficient for having a Ca/P ratio from about 0.5 to about 5, preferably from about 1 to about 2. More preferably, one or more calcium phosphate salts (for example calcium orthophosphate) and calcium salts (calcium hydroxide) are added in an amount sufficient for having a Ca/P ratio from about 1.5 to about 2, preferably from about 1.67 to about 1.95.

According to an advantageous embodiment, the solution of fibrin or fibrinogen materials used in the process of the invention has a low albumin content, for example the solution contains less than about 5% by weight of albumin, with respect to the weight of fibrin or fibrinogen material.

According to another embodiment, particles having the porous structure of the invention are added to the solution of fibrinogen or fibrin material before the polymerization with at least partial cross-linking and/or during the polymerization with at least partial cross-linking.

According to a detail of a preferred embodiment, at least a compound selected from the group consisting of: processing aids (such as lubricant, plastifying agent, surfactant, viscosity reducing agent, etc.), fibers, polymers, copolymers, antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, growth factors for heparin bond, substances against cholesterol, pain killers, collagen, osteoblasts, drugs, etc. and mixtures thereof is added to the solution before the polymerization with at least partial cross-linking, and/or during the polymerization with at least partial cross-linking, and/or after the polymerization with at least partial cross-linking, and/or before the lyophilization. According to another embodiment, after the lyophilzation or a partial lyophilization, the at least partly cross-linked fibrin or fibrinogen material is mixed with a compound selected from the group consisting of: additive (for example comprised within the wall of the channels or cells of the structure) or is provided with a layer containing at least an additive, said additive being selected from the group consisting of processing aids (such as lubricant, plastifying agent, surfactant, viscosity reducing agent, etc.), fibers, polymers, copolymers, antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_2$–$C_{24}$ fatty acids, drugs, etc. and mixtures thereof.

It has been observed that the use of different calcium inhibiting agents have different effects on the volume variation of the structure during the hydration, and it is possible to use inhibiting agents with a positive volume variation during the hydration (volume increase of the structure) and inhibiting agents with a negative volume variation during the hydration (volume decrease of the structure) in amounts sufficient for obtaining a structure with substantially no volume variation during the hydration.

According to a specific detail of an embodiment of the process, after the partial polymerization with at least partial cross-linking of the fibrin or fibrinogen materials, but before the lyophilization step, the polymerized material (that advantageously forms a hydrogel) is submitted to a treatment (advantageously a mechanical treatment, such as a centrifugation) for removing part of excess water present in the material. The treatment is preferably a treatment not altering the chemical links of the polymerized, partly cross-linked material.

In the process of the invention, the fibrin or fibrinogen material is polymerized with a partial cross-linking. For example, the partial cross-linking is a cross-linking of less than about 50% by weight of the fibrin molecules, more preferably from about 0.5 to about 40% by weight of the fibrin molecules, preferably from about 1 to about 20% by weight of the fibrin molecules.

The fact that the fibrin or fibrinogen material is polymerized with a partial cross-linking can be observed by an electropheris SDS-polyacrilamide gel by the absence of the γ-band detectable in the Fibrin-fibrinogen starting material and by the intensity of the γ-γ band of the material after polymerization. The electrophoresis of reduced protein using 4–15% gradient polyacrilamide gels showed that for fibrin with complete cross-linking, there is no residual monomeric γ chains remaining and the cross linked fibrin showed characteristic β and γγ polymer chains as prominent (substantially no α chain is remaining).

The intensity of the γ-γ band is correlated to the cross-linking rate. It means that, when the intensity of the γ-γ band is low, the cross-linking rate of the fibrin or fibrinogen is low. In order to determine the cross-linking rate in the process of the invention, solutions with different fibrinogen content were cross-linked not in presence of calcium inhibiting agent and the intensity of the γ-γ band of the cross-linked fibrinogen solutions is determined by SDS analysis for having a reference. The intensity of the γ-γ band of the fibrinogen polymerized in presence of the calcium blocking agent is then compared with the reference, so as to determine the amount of cross-linked fibrinogen, and therefore the percent of cross-linked fibrinogen and the percent of polymerized (not cross-linked) fibrinogen. The amount of cross-linked fibrinogen in the structure of the invention is considered as being the amount of fibrinogen cross-linked not in presence of a calcium blocking agent (in a reference solution) having substantially the same intensity for the γ-γ band.

The lyophilization step of the solution can be carried out after placing the solution in a mould so as to give a shape to the lyophilized product. It is also possible to adjust the desired shape of the lyophilized product after lyophilization and/or after hydration thereof.

The fibrin-fibrinogen material used in the process of the invention can possibly be a recombinant fibrin-fibrinogen or a mixture of a recombinant fibrin-fibrinogen with a natural fibrin-fibrinogen material. The thrombin used can be thrombin of natural origin, recombinant thrombin, or mixture thereof.

The polymerization, with advantageously partial cross-linking, of the fibrin-fibrinogen material can possibly be carried out in presence of collagen, recombinant collagen, fibronectin, recombinant fibronectin, albumin, recombinant albumin, factor XIII, recombinant factor XIII, interactive biomaterials (such as RGD collagens) and mixtures thereof. The collagen is, for example, a photo activateable or light activateable recombinant collagen.

The thrombin is, for example, a cage thrombin, a light activateable thrombin, a recombinant thrombin, etc. According to a preferred embodiment, the thrombin is mixed with a calcium inhibiting or blocking agent, especially a anticoagulant.

It is also possible to add and mix collagen, recombinant collagen, fibronectin, recombinant fibronectin, albumin, recombinant albumin, factor XIII, recombinant factor XIII, interactive biomaterials (such as RGD collagens) and/or mixtures thereof to the hydrogel of fibrin-fibrinogen before its lyophilization.

Specific processes are:

formation of a hydrogel of fibrin-fibrinogen material according to the process of the invention, addition of bone chips to the hydrogel, lyophilization;

formation of a hydrogel of fibrin-fibrinogen material according to the process of the invention, addition and mixing of collagen (preferably photo activable), lyophilization;

formation of a hydrogel of fibrin-fibrinogen material according to the process of the invention, addition and mixing of collagen (preferably photo activable) and bone chips, lyophilization;

formation of a hydrogel of fibrin-fibrinogen material according to the process of the invention, addition and mixing of a hydrogel of collagen and preferably of bone chips, lyophilization.

The hydrogel prepared according to the process of the invention, possibly after a first treatment for removing an excess of water, can be spray-freeze dried, sprayed in drops which are thereafter freeze dried, freeze IR dried, so as to prepare particles having the structure of the invention, for example substantially spherical particles having a particle size or diameter of less than 2 mm, for example a particle size from about 500 μm to about 1 mm. The particle size distribution can be adjusted as required by adjusting the parameter of the spray-freeze drying and/or the spraying.

The invention relates also to a support, advantageously a metal support, preferably a titanium containing support provided with a layer having the structure of the invention or a layer comprising particles having the structure of the invention. The support is possibly porous.

Such a support can be prepared, for example, by one of the following processes:

In a first process, the support is contacted with the solution containing the fibrin or fibrinogen material and the calcium inhibiting or blocking agent as disclosed in the process of the invention. Thereafter, the support in contact with the solution is lyophilized so as to obtain a support (for example a titanium containing support) coated with a porous structure as disclosed in the porous structure of the invention. When the support is porous, pores of the support can be filled with a product having the structure of the invention.

In a second possible process, particles having the porous structure of the invention are sprayed on a support (for example a titanium containing support) coated with an adhesion layer, for example a fibrin based layer.

In a third possible process, particles having the porous structure of the invention have been mixed with an adhesive composition, for example a biocompatible glue, such as a fibrin glue, and the adhesive composition with the particles is used for coating the support, preferably a titanium containing support (for example by spaying the composition or by brushing the composition on the support).

According to still a further possible process, lyophilized particles having the structure of the invention are mixed with thrombin and/or calcium containing compound, the mixture possibly mixed with an adhesive or liquid glue being used for coating the titanium containing support (for example provided with a glue layer). The thrombin used is for example an inactivated thrombin, for example a thrombin that is light-activated.

A further object of the invention is therefore a mixture of particles of fibrin and/or fibrinogen materials with inactivated thrombin, said mixture possibly containing further additives, such as drugs, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, proteins, interferons, hormones, polysaccharides, genetic materials, proteins promoting or stimulating the growth and/or attachment of endothelial cells on the cross-linked fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_{12}$–$C_{24}$ fatty acids, drugs, pain killers, etc., and mixtures of said compounds or a solution containing at least one of said compound.

The structure of the invention is advantageously provided with cells.

The invention relates also to a kit suitable for forming a bone substitute, said kit comprising a first chamber containing a product having the structure of the invention, and a second chamber containing an aqueous solution containing at least BMP (bone morphology proteins). The product having the structure of the invention is hydrated with the solution before its use as a bone substitute.

For example, the kit comprises a blister or chamber and a part equipped with a luer lock system to be fixed to syringe.

EXAMPLES

Example 1

Figure 1:
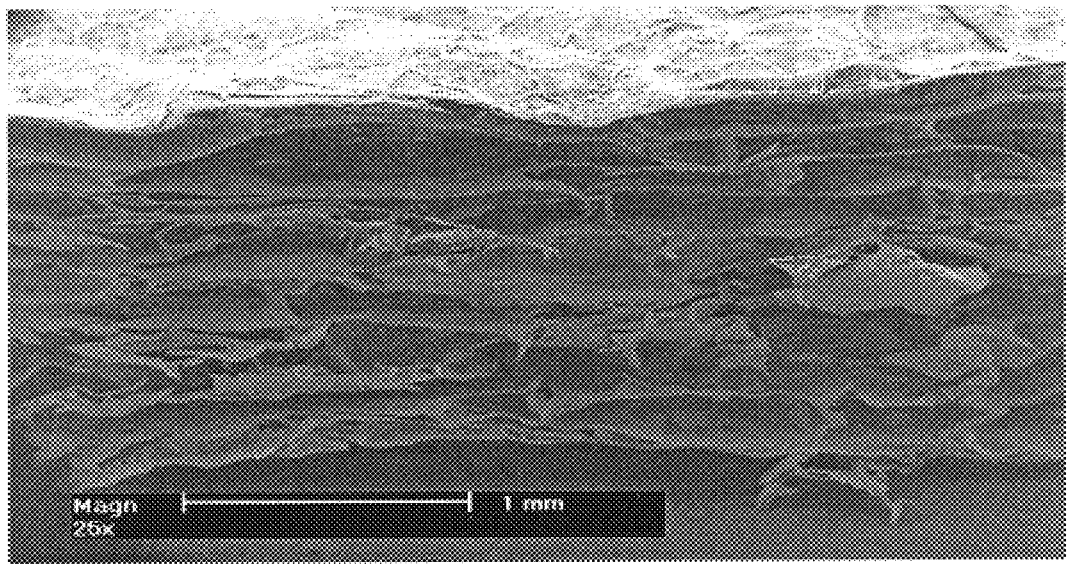
FIG. 1 is a cross section view of a structure of the invention with use of PBS and after the lyophilization step.

To an aqueous fibrin solution containing 100 mg fibrin-fibrinogen/ml and having a pH of 7.1, an albumin content of less than 5% by weight of the weight of fibrin-fibrinogen, a factor XIII content of about 0.1 IU per mg fibrin-fibrinogen, 1 ml of a phosphate buffer solution (PBS) per ml of the aqueous fibrin solution ( composition of the PBS buffer solution : NaCl 8 g/l; KCl 200 mg/l; $Na_2HPO_4$ 1.15 g/l; $KH_2PO_4$ 200 mg/l) was added. The pH of the so prepared buffered fibrin solution was 7.2, while the fibrin-fibrinogen content was 50 mg/ml. A solution containing 20 IU thrombin per ml (the thrombin solution was reconstituted from thrombin powder and PBS) was added to said buffered solution at the rate of 1 ml thrombin solution per ml of fibrin solution. When using this amount of PBS, the clotting time of the reaction mixture was 430 seconds at 37° C., said clotting time being measured by using the apparatus "Dade Behring BFT II"® (version 1.2—date of issue of the technical book October 1999) of Dade Behring, Germany. In said apparatus, a plastic vial containing 0.5 ml of the solution was placed in the apparatus for ensuring an agitation (by means of the stir bar) and a substantially constant temperature of the sample to be tested. The apparatus enables the detection of any small whirls or clots present in the sample due to the stirring bar.

After 5 minutes reaction at 20° C., the solution containing polymerized and partially cross-linked fibrin was lyophilized at a temperature of −50° C. and at a pressure of about $0.4 \times 10^5$ Pa.

The solution containing fibrin-fibrinogen material and thrombin had an osmolarity of about 450 mosm, said osmolarity being measured by using the apparatus FISKE 2400

OSMOMETER (Fiske Associates) according to the following method:

A sample is supercooled several degrees below the freezing point. The heat of fusion liberated allows sample temperature to rise a temporary "liquid-solid" equilibrium. Said equilibrium is by definition the freezing point of the solution. The freezing point is related to stols to allow determination of osmolarity. The osmolarity is equal to the osmoles of solute per Kg of pure solvent.

After polymerization and partial cross-linking of fibrin, a hydrogel was formed, said hydrogel having an optical density (measured at a wavelength of 800 nm) of 0.255 AUFS (absorbance unit full scale).

Figure 3:
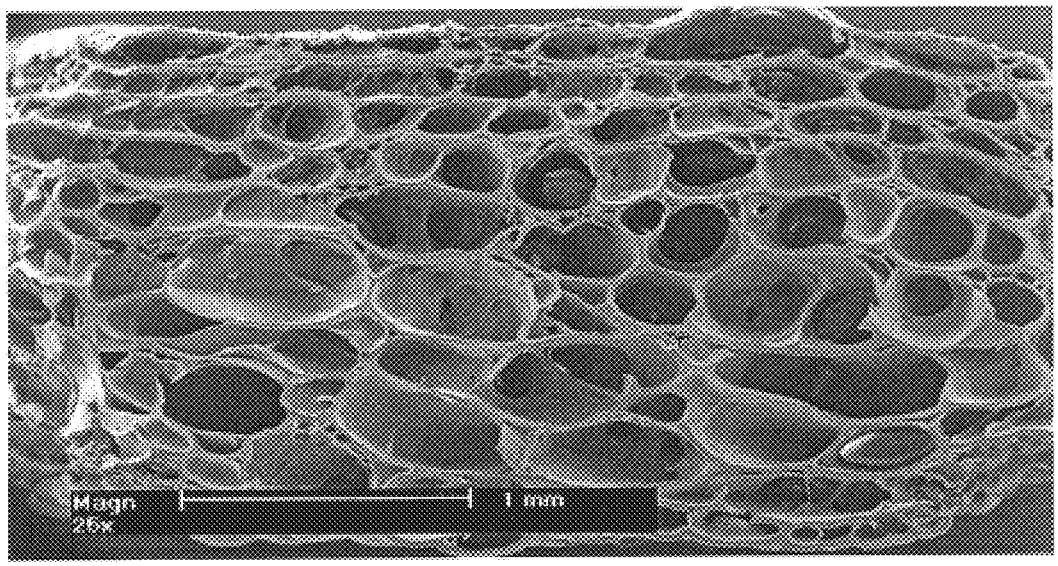
FIG. 3 is a cross section view of the structure of FIG. 1, after hydration.

FIG. 1 is a cross section view (scanning electronic microscope, SEM Philips XL20) of the structure obtained after lyophilization, while FIG. 3 is a cross section view of the structure after hydration thereof in an aqueous bath.

Figure 2:
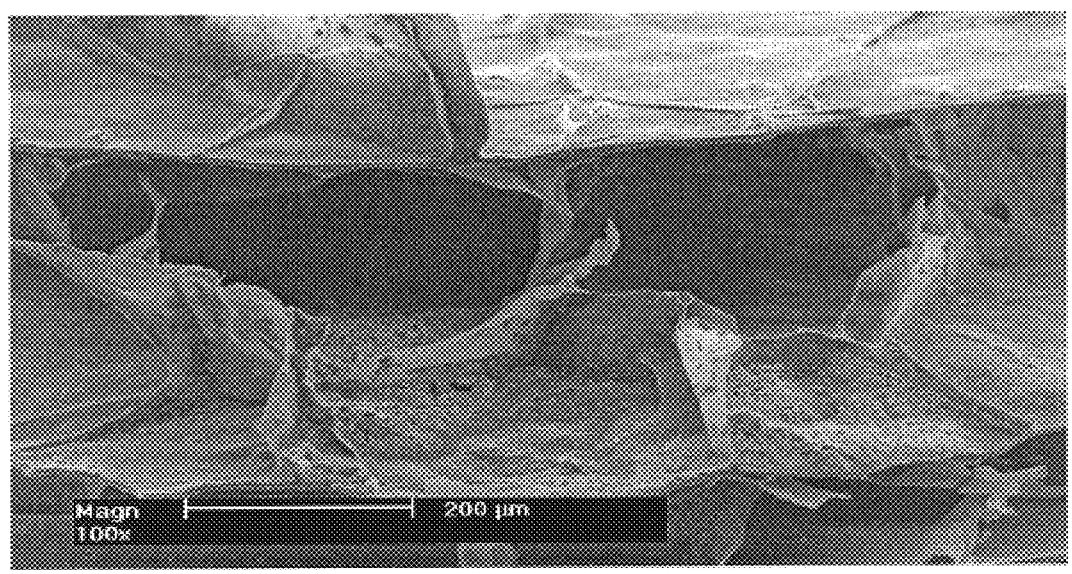
FIG. 2 is an enlarged view of the structure of FIG. 1.
Figure 4:
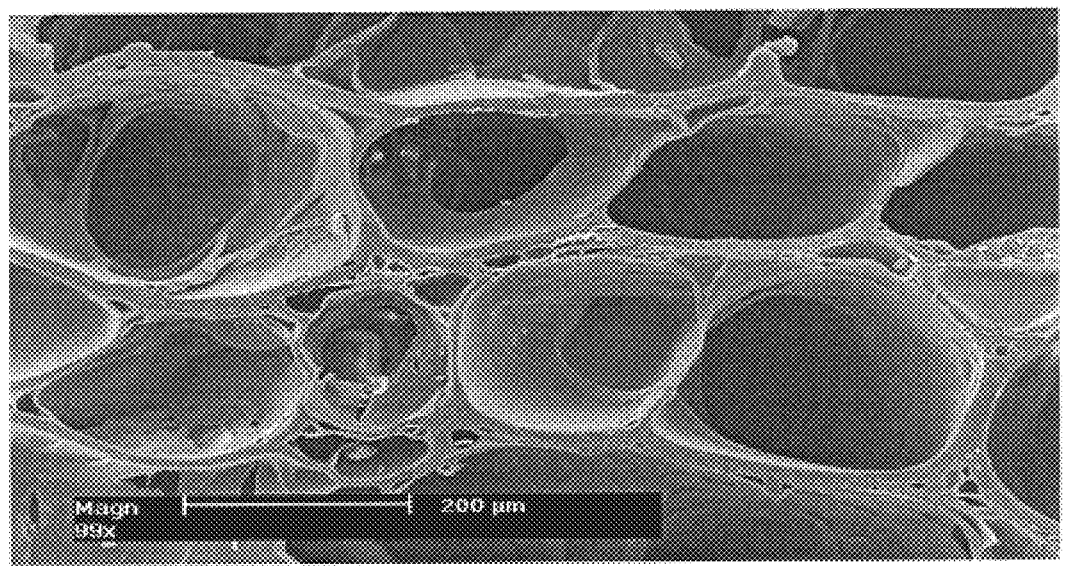
FIG. 4 is an enlarged view of the structure of FIG. 3.

As it can be seen from FIGS. 2 and 4, which are enlarged views respectively of FIG. 1 and FIG. 3, channels are formed in the structure, the channel having a substantially central axis parallel to the skin surface of the structure. When cutting the structure in a plane substantially perpendicular to the central axis of the channels (as shown in the views), it can be seen that after hydration, the channels have an open surface of about 200 $\mu$m×150 $\mu$m, said channels being at least partly separated therebetween by a wall with a thickness of about 10 $\mu$m. After hydration, the structure in cross section was similar to a honeycomb structure. After hydration, the open surface area of the channels is quite circular and regular.

When hydrated, it was observed a decrease of the thickness of the porous product, i.e., the ratio volume of the porous structure in its substantially dry form/volume of the porous structure in its hydrated form was about 1.5. In its hydrated form, the shape of the cells of the honeycomb structure was more regular.

The structure had a compression strain of less than 7% for the first and second compression cycle, said resistance being measured by the following method:

A sample of the structure having a diameter of 5 mm and a thickness of 0.921 mm was submitted to a compression of 2500 mN (between two parallel plates and with a compression ramp of 500 mN/minute). The strain or height difference of the sample due to the compression (expressed in %) was measured. After release of the compression (recovery step), the sample was subjected again to a compression of 2500 mN (with a compression ramp of 500 mN/minute) and the strain was measured back at 2500 milli Newtons.

The creep modulus was also measured at the end of the first compression cycle to 2500 mN and at the end of the second compression cycle to 2500 mN.

The measured creep modulus at the end of the first compression cycle and at the end of the second compression cycle was from $1.6 \times 10^6$ Pa to $2.0 \times 10^6$ Pa.

The strain (%) and creep modulus were measured at 20° C. by using a PERKIN-ELMER, Thermal analysis System.

As the PBS buffer contains phosphate, the structure was enriched in P. The weight ratio P/fibrin-fibrinogen material of the structure is about 0.3%. The apparent density of the structure is about 0.14 g/cm$^3$, while the surface area of the structure is less than 1 m$^2$/g.

The structure was washed, under aseptic conditions, with sterile and pyrogen-free water and can possibly further be sterilized by methods known per se, for example by $\gamma$-radiation (35 KGray).

Example 1b

Example 1 was repeated except that 2 ml of PBS was added per ml of the fibrin-fibrinogen material, whereby the final fibrin solution contained 16.6 mg fibrin-fibrinogen per ml.

The osmolarity of the solution containing fibrin-fibrinogen material and thrombin was greater than about 500 mosm.

After lyophilization, the strain and creep modulus were determined by using the method of example 1. The strain was of 6.5% for the first and second cycle of compression up to 2500 mN. Said strain was even kept for successive compression cycles (for example for 10 or even more successive compression cycles).

The creep modulus was equal to about $1.85 \times 10^6 - 1.87 \times 10^6$ Pa for the first and second cycle of compression up to 2500 mN. Said modulus was even kept for successive compression cycles (for example for 10 or even more successive compression cycles).

Figure 19:
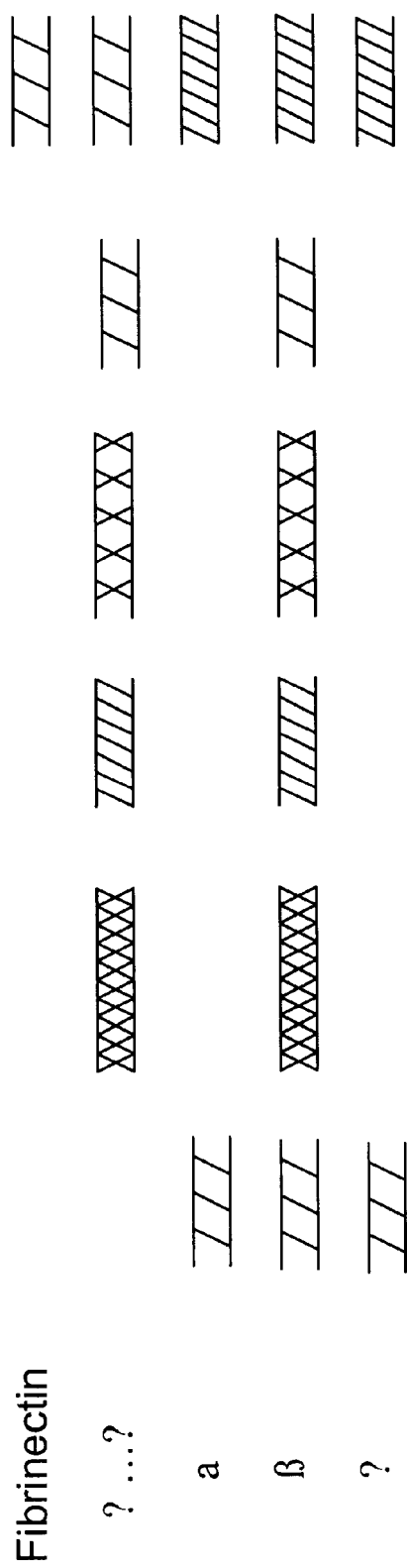
FIG. 19 is a SDS electrophoresis.

FIG. 19 is a schematic view of a SDS electrophoresis using 4–15% gradient polyacrylamide gels. In FIG. 19, A is the SDS electrophoresis of fibrinogen (before its reaction), said electrophoresis showing the presence of $\alpha$, $\beta$, and $\gamma$ bands. B1,B2,B3,B4 are respectively the electrophoresis of fibrinogen cross-linked (reaction with thrombin, without addition of calcium blocking agent). The electrophoresis B1,B2,B3,B4 is essentially characterized by a $\gamma$-$\gamma$ band and a $\beta$ band. The intensity of the bands decrease with the fibrinogen content of the solution B1,B2,B3,B4 analyzed. In the present case the fibrinogen content of the solution is decreased from B1 to B4 (B1:fibrinogen content 2 mg/ml, B2: fibrinogen content 1 mg/ml, B3: fibrinogen content 0.5 mg/ml, B4: fibrinogen content 0.25 mg/ml, while the amount of thrombin used remains the same).

The electrophoreris C is the electrophoresis of the gel formed by the reaction of fibrinogen in presence of the calcium blocking agent (using the thrombin amount used for preparing product B). Said electrophoresis is essentially characterized by a fibronectin band, $\alpha$, $\beta$, and $\gamma$ bands and by a $\gamma$-$\gamma$ band of low intensity. By comparing the intensity of the $\gamma$-$\gamma$ band of product C with the intensity of the $\gamma$-$\gamma$ band B1,B2,B3,B4, it is possible to determine the amount of fibrinogen cross-linked present in the product C. In the present case, the amount of fibrinogen cross-linked in product C is substantially equivalent to the amount of fibrinogen of product B4, i.e., 0.25 mg fibrinogen per ml. As the fibrinogen content of the solution or gel C was equal to 16.6 mg/ml, it means that about 0.25 mg/16.6 mg, i.e., about 1–2% of cross-linking or of cross-linked fibrinogen.

For the electrophoresis analysis, the products A,B,C were dissolved in SDS/DTT/Tris solvent.

Example 2 (Comparative)

Figure 5:
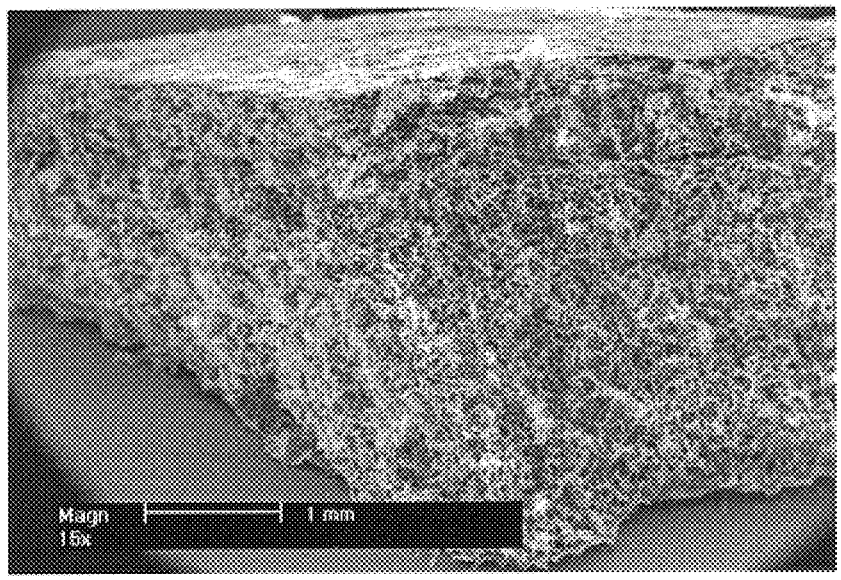
FIG. 5 is a cross section view of a structure obtained without use of PBS after the lyophilization step.
Figure 6:
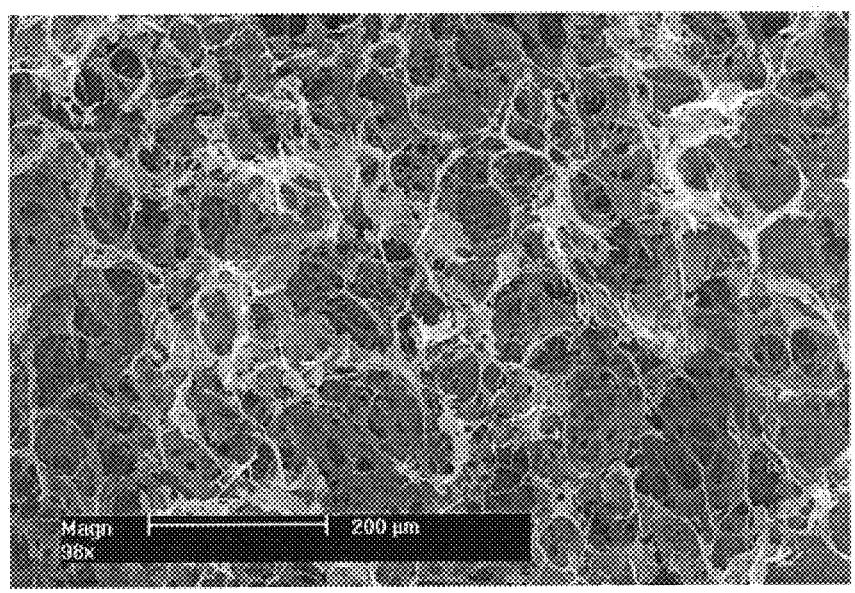
FIG. 6 is an enlarged view of the structure of FIG. 5.
Figure 7:
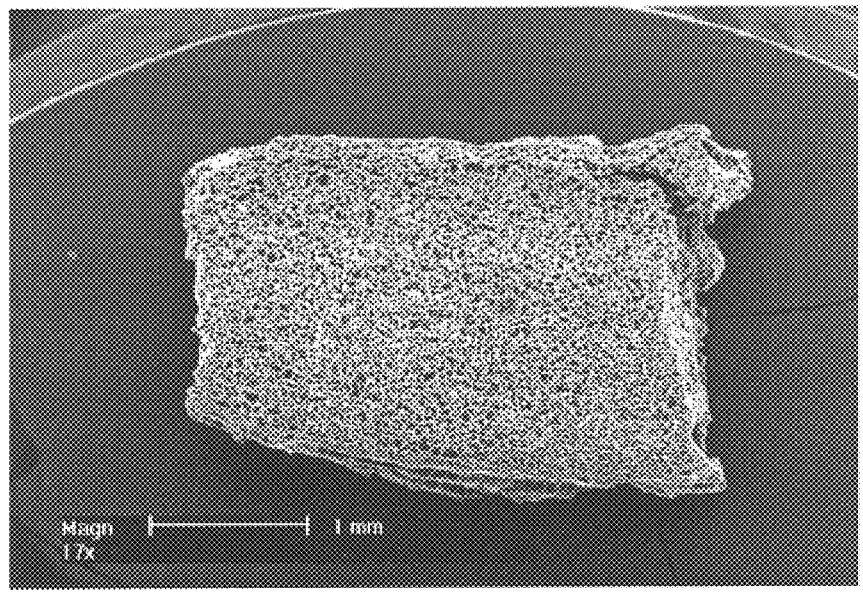
FIG. 7 is a cross section view of the structure of FIG. 5, after hydration.
Figure 8:
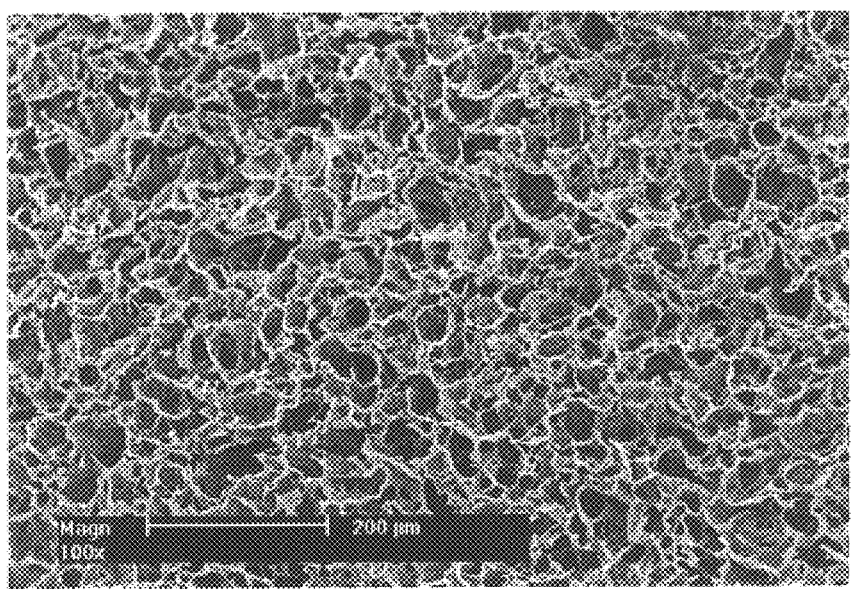
FIG. 8 is an enlarged view of the structure of FIG. 7.

Example 1 was repeated, except that no phosphate buffer was added. The structure obtained after lyophilization was a porous and compressible material. FIGS. 5 and 6 are cross section views (electron microscope) of the structure, while FIG. 7 and 8 are cross section views of the structure after hydration of the structure in an aqueous bath.

The material had a compression strain at 2500 mN of more than 10% and a creep modulus lower than $1.5 \times 10^6$ Pa. The cells or channels of the structure are quite irregular and not homogeneous. The size of the cells or open surface of the channels is 50×50 $\mu$m$^2$. When hydrating the lyophilized structure, the volume of the structure was increased by a factor of more than 2.

Example 3

Example 1 was repeated, except that 1 ml of PAS per ml of fibrin solution (PAS being a buffer solution containing 2.94 g/l sodium citrate, 6.75 g/l sodium chloride and 4.08 g/l sodium acetate) instead of PBS.

Figure 9:
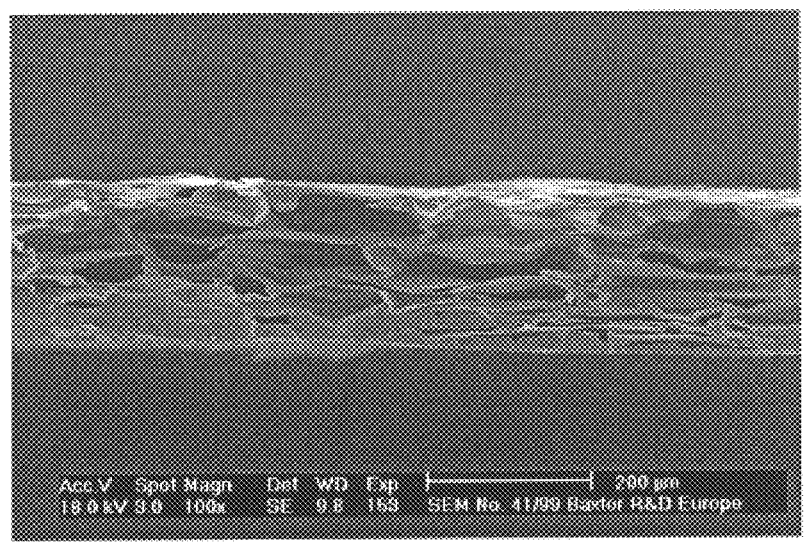
FIG. 9 is a cross section view of a structure of the invention with use of PAS, after lyophilization.
Figure 10:
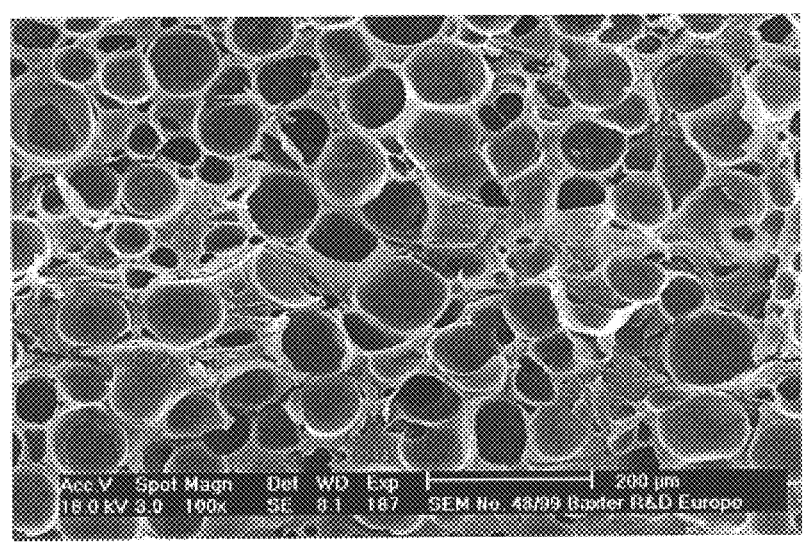
FIG. 10 is a cross section view of the structure of FIG. 9, after hydration.

FIG. 9 is a cross section view of the structure after lyophilization, while FIG. 10 shows in cross section the structure of FIG. 9 after hydration. The open area of the channels after hydration was about 10000 $\mu m^2$. A quite regular structure was obtained.

During the hydrating, a volume increase of the structure was observed. The ratio volume of the hydrated structure/ volume of the structure after lyophilization was about 1.5.

Example 4 (Comparative)

Figure 11:
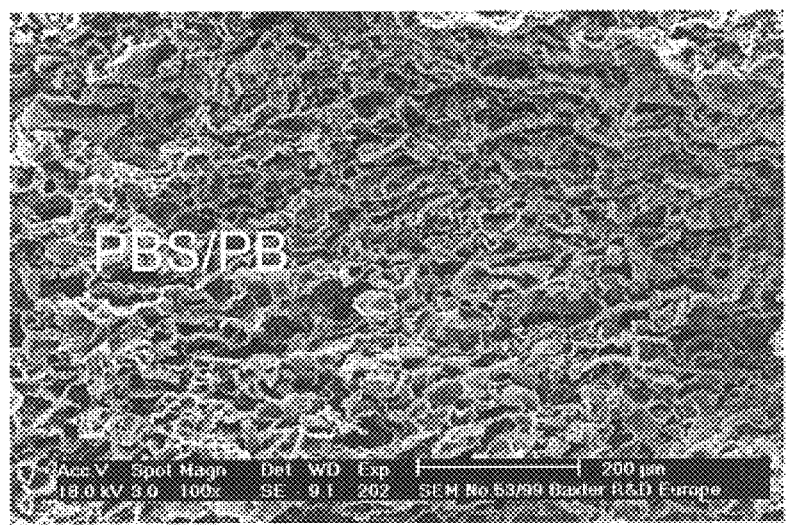
FIG. 11 is a cross section view of a structure prepared when using $CaCl_2$ instead of PBS, after lyophilization.
Figure 12:
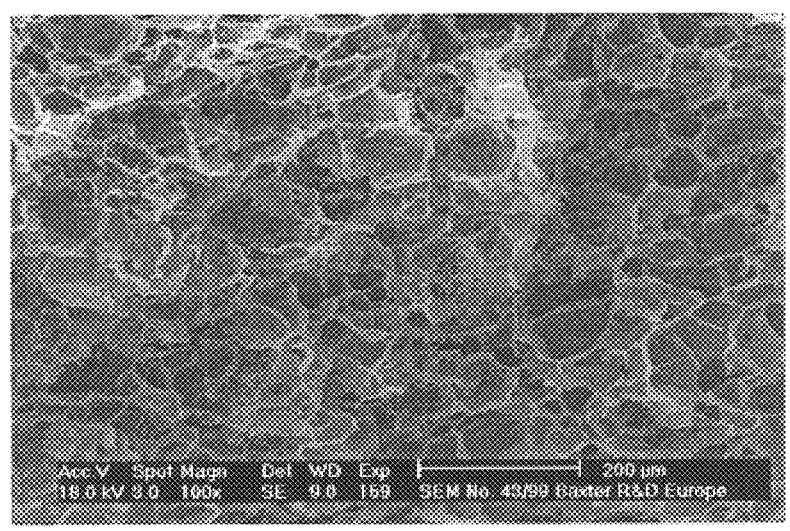
FIG. 12 is a cross section view of the structure of FIG. 11 after hydration.

Example 1 was repeated, except that 1 ml of a solution containing 5 mg $CaCl_2$/ml per ml of fibrin solution was used instead of PBS. FIG. 11 shows in cross section the structure after lyophilization, while FIG. 12 shows in cross section the structure of FIG. 11 after hydration.

Figure 13:
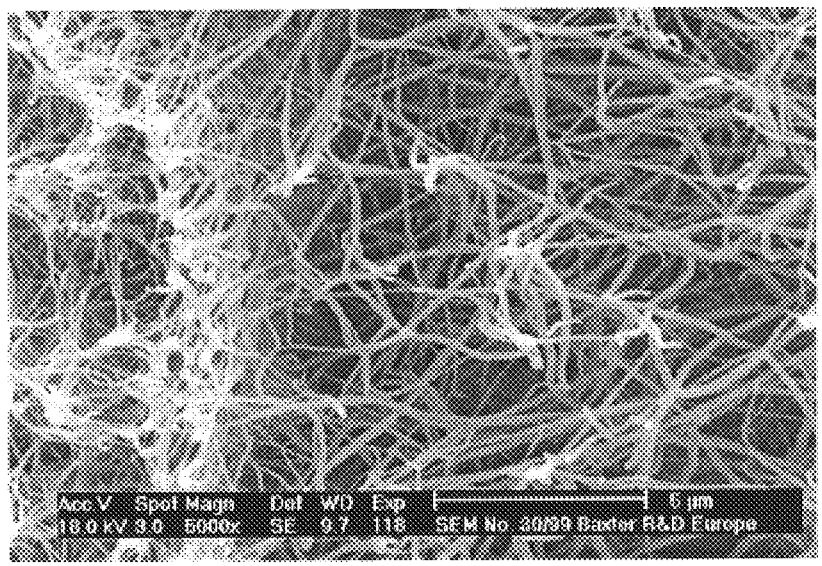
FIG. 13 is an enlarged view of the hydrogel used for the preparation of the structure of FIG. 11 (structure before the lyophilization)
Figure 14:
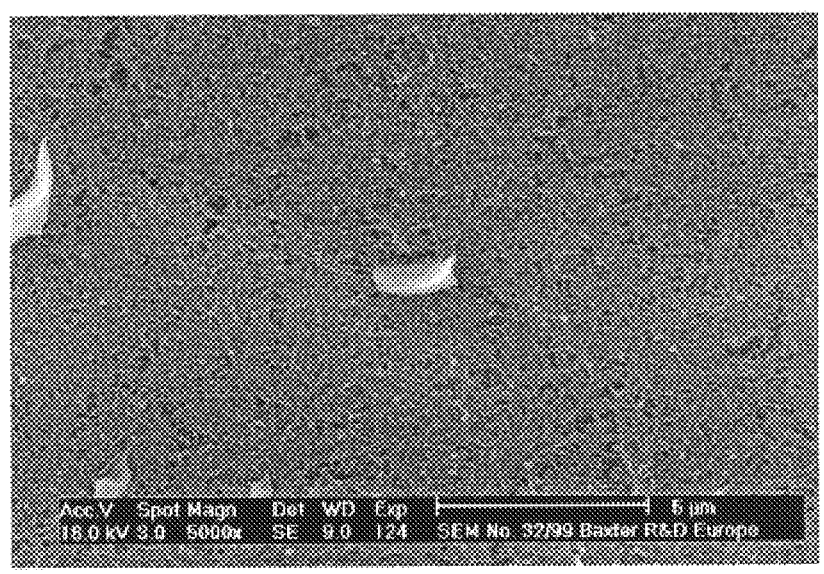
FIG. 14 is an enlarged view of the hydrogel used for the preparation of the structure of FIG. 5 (structure before the lyophilization)
Figure 15:
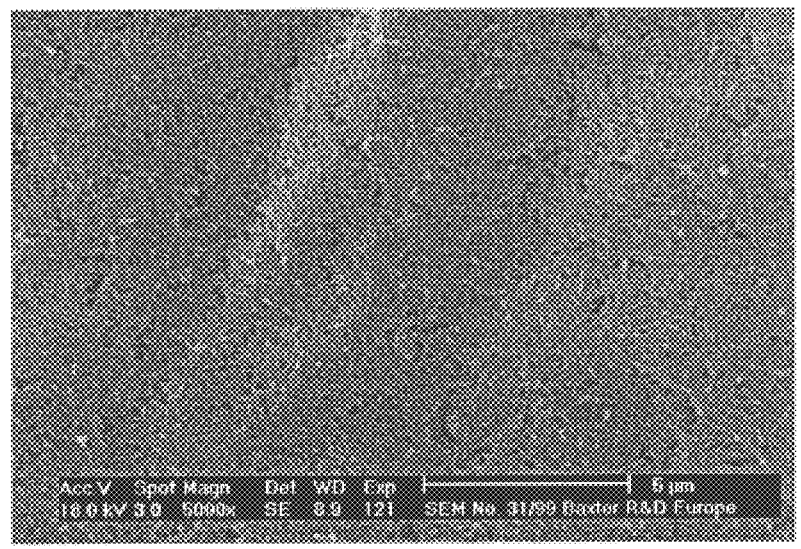
FIG. 15 is an enlarged view of the hydrogel used for the preparation of the structure of FIG. 9 (structure before the lyophilization)
Figure 16:
FIGS. 16 to 18 are schematic views, in cross-section, of supports provided with a layer having the structure of the invention or containing particles of the invention.
Figure 17:
Figure 18:
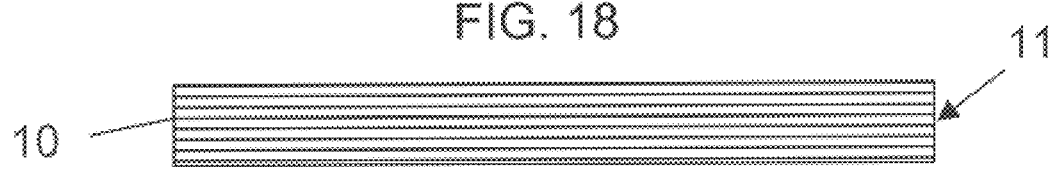

As it can be seen from these figures, the structure is very irregular. A view on a still enlarged scale (FIG. 13) shows that the structure after hydration substantially corresponds to a net of fibers linked therebetween. FIGS. 14 and 15 show on enlarged scale a surface of the structure obtained when using respectively PBS and PAS instead of $CaCl_2$. When comparing said FIGS. 14 and 15 with the FIG. 13, it is clear that the structure obtained when using PBS or PAS is quite different from the structure obtained by $CaCl_2$ alone.

Said comparative example shows the importance of the presence of a calcium inhibiting agent in the fibrin solution.

Examples 5 to 9

Example 1 was repeated, except that the amount of phosphate buffer solution (PBS) varied and that the fibrin content of the solution was varied. The following table gives the fibrin content of the solution, as well as the amount of PBS (ml) used per ml of fibrin solution with a fibrin content of 100 mg/ml.

| Example | 5 | 6 | 7 | 8 | 9 |
|---|---|---|---|---|---|
| Fibrin content (mg/ml) | 25 | 16.6 | 12.5 | 10 | 8 |
| PBS ml per ml of solution of fibrin with a content of 100 mg/ml | 3 | 5 | 7 | 9 | 11.5 |

Examples 10 to 16

Example 1 was repeated, except that the amount of thrombin and/or the amount of PBS were different.

| | Example | | | | | | |
|---|---|---|---|---|---|---|---|
| | 10 | 11 | 12 | 13 | 14 | 15 | 16 |
| Fibrin-fibrinogen mg/ml of the final solution | 50 | 50 | 25 | 25 | 25 | 12.5 | 12.5 |
| Thrombin IU/ml of the final solution | 1 | 2 | 1 | 2 | 10 | 1 | 2 |
| PBS ml per ml of solution of fibrin with a content of 100 mg/ml | 1 | 1 | 3 | 3 | 7 | 7 | 7 |

Examples 17 to 26

Example 1 was repeated, except that other calcium blocking agent were used instead of PBS.

| Example | Calcium blocking agent |
|---|---|
| 17 | Sodium citrate |
| 18 | 50% PAS + 50% PBS |
| 19 | Sodium phosphate (hexa meta phosphate) |
| 20 | Sodium ortho phosphate |
| 21 | Diethylene glycol |
| 22 | Potassium citrate |
| 23 | Lidoflazine |
| 24 | Polyacrylate |
| 25 | Sodium salt of tannic acid |
| 26 | Polymethacrylate |
| 27 | Potassium citrate |
| 28 | Ethylene diamine tetra acetic acid |

The product of example 18 had a structure having a volume in its substantially dry form which is substantially equal to the volume in its hydrated form.

Examples 29 to 40

Example 1 has been repeated, except that additives have been added to the solution before its lyophilization.

The following table gives the additives and the quantity of additives (mg/ml) added.

| Example | additive | Amount mg/ml of solution |
|---|---|---|
| 29 | Bone growth factor BMP | 1 |
| 30 | Osteoblast | 1 |
| 31 | Indomethacin (anti-inflammatory) | 3 |
| 32 | Paracetamol (pain killer) | 3 |
| 33 | Glycerol | 5 |
| 34 | A frazzled polypeptide (compound preventing a graft rejection) | |
| 35 | Collagen (for increasing the cell attachment) | 5 |
| 36 | Calcium glycerophosphate | 2 |
| 37 | morphine | 1 |
| 38 | sulfamide | 2 |
| 39 | sodium polyethylene | 3 |
| 40 | Zocor ® | 2 |

The structure of the invention can be used in the preparation of a glue and a cement.

Example 41

The structure of example 1 was submitted to a mechanical grinding so as to obtain, after sieving, particles with a grain size of about 600 to 1000 μm. 1 g of said particles (with the structure of Example 1) were added to a known fibrin glue (1 ml), known as Tisseel®), glue sold by Baxter Hyland Immuno. The glue with particles was excellent for filling holes and recess in bones, etc.

Tisseel is in fact a fibrin glue sold as a kit. The fibrin particles are then advantageously added to the bottle containing the sterile water and/or to the bottle containing the thrombin.

The structure of the invention can be used for the preparation of multilayer structure.

Example 42

A slice of the structure of example 1(5 mm thick) was placed near the upper and free face of the liquid composition of example 4. After the reaction of the liquid composition for forming fibrin bounds, the composition and slice were lyophilized so as to obtain a multilayer structure comprising a first layer with the structure of example 1 and a second layer having the structure of example 4.

The multilayer structure has a quite rigid structure with large pores on one face and a layer of a net of fibrin bound. Such a multilayer structure can be used in bioreactor, as the large pores are suitable for the attachment of cells, endothelial cells, while the net of fibrin is advantageous for avoiding the passage of cells.

Examples 43 to 50

On a cut of the structure of example 1, a composition was applied for covering at least partly the slice of example 1 and for forming a layer on the cut.

The following table gives the composition of the layer covering the structure of the example 1.

| Example | Covering layer |
| --- | --- |
| 43 | Collagen layer |
| 44 | Elastin layer |
| 45 | Fibronectin layer |
| 46 | Laminin layer |
| 47 | Tenascine layer |
| 48 | Cellulose layer |
| 49 | Dextran layer |
| 50 | Collagen + Tenascin layer |
| 51 | Heparan sulfate layer |
| 52 | Dermartan sulfate layer |
| 53 | Chondroitine sulfate layer |
| 54 | Fibrin - fibronectin layer |
| 55 | Collagen - fibronectin layer |

Example 56

The sterile and pyrogen-free structure of example 1 can be used as a support for proteins for removing a substance from the blood of a human subject.

The coupling of the protein(s) on the support can be performed in accordance to the method disclosed in U.S. Pat. No. 5,817,528, the content of which is incorporated by reference.

The protein coupled to the structure is for example the protein A.

Other proteins which could be coupled to the structure are: Streptococcus Protein G, Anti-human immunoglobulin antibodies, anti-LDL antibodies, etc.

The structure provided with the protein(s) can be used in a column for removing immunoglobulin G or M or A or E, LDL or lipoprotein A.

Example 57

The structure of example 1 after sterilization was filled with a drug or an active agent.

For filling, the structure was immersed in a solution containing the drug or active agent in a dissolved form. Thereafter the solvent is removed for example by lyophilization. The preferred solvent is water or an aqueous medium (aqueous medium containing a polyethylene glycol, for example a PEG with a low molecular weight, PEG 400, PEG 600, etc.).

Example of possible active agents or drugs are: antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, proteins, interferons, hormones, polysaccharides, genetic materials, proteins promoting or stimulating the growth and/or attachment of endothelial cells on the cross-linked fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_{12}$–$C_{24}$ fatty acids, drugs, pain killers, etc., and mixtures thereof.

Example 58

A structure was prepared as in example 1. However before the lyophilization step, the reaction mixture was placed on a filter (paper filter with a pore size of about 251 μm) so as to remove a water excess. The gel remaining on the paper filter was then lyophilized at −50° C. and at pressure of less than $0.4 \times 10^5$ Pa, so as to obtain a porous structure with a substantially homogeneous layer of fibrin.

Example 59

Example 1 has been repeated for the preparation of a hydrogel. However, in example 59, half of the volume of PBS has been replaced by a PAS buffer solution.

The hydrogel was used for coating a titanium containing support. The coating had a substantially constant thickness.

The support provided with the hydrogel coating was submitted to a lyophilizing step as disclosed in example 1. After said lyophilization step, the titanium containing support 1 was provided on its both sides, with a porous layer 2.

Due to the use of a mixture of PAS and PBS buffers, the volume of the porous layer 2 after its hydration was substantially equal to the volume of the layer before its hydration.

Example 60

The hydrogel of example 59 was lyophilized as disclosed in example 1. The porous cake obtained after lyophilization was ground in particles 4 having a size lower than 200 μm.

The titanium containing support was provided with a collagen layer 3 on which particles 4 have been sprayed.

Example 61

Example 1 has been repeated for preparing porous layers having a thickness of about 2 mm thick. Ten layers 10 were superimposed so as to form a multi layer structure 11. The multi layer structure was pressed so as to reduce the total thickness of the multi layer to about 2 mm. The pressed multi layer structure had a higher density, had a compact structure, had pores with a size lower than 10 µm, and had a high hardness (a cut with a knife, for example with a special cutter for samples to be examined with an electron microscope, was difficult to make on the face of the structure).

Example 62

Particles of the example 59 were pressed in a molds with a pressure of 500 kg to 5 tons per cm², in particular at a pressure 1 ton/cm², 2 tons per cm², 3 tons per cm² and 4 tons per cm².

A solid cake was obtained. Said cake, when hydrated, increased highly of volume, and thereafter the cake started to disintegrate into particles.

Examples 63 to 67

Example 1 has been repeated except that the hydrogel formed is first submitted to a mechanical withdrawal of water, so as to form a compacted hydrogel. The compacted hydrogel was then submitted to the lyophilization step as disclosed in example 1. The mechanical withdrawal of water was carried by placing the hydrogel on a filter and by submitting the hydrogel placed on the filter to a centrifugation. The centrifuged hydrogels of examples 63 to 67 had lost respectively 5% by volume, 10% by volume, 15% by volume and 20% by volume. A loss of 5% by volume means that a volume of water corresponding to 5% of the volume of the initial hydrogel (before lyophilization) passed through the filter and was therefore removed from the hydrogel.

It has been observed that, when adjusting the amount of water present in the hydrogel before its lyophilization, it was possible to modify the ratio volume of the porous structure in its substantially dry form/volume of the porous structure in its hydrated form. In the present case, when removing about 15% by volume water, the ratio could be reduced to about 1–1.2.

Examples 68 to 76

Example 1 has been repeated except that bone particles having an average particle size (average in weight) from about 100 µm to about 2 mm were added.

The following table gives the type and amount of bone chips or particles added to the solution of fibrin-fibrinogen material of example 1 after the polymerization with partial cross-linking (forming a hydrogel).

| example | Average size of the bone particles (µm) | 90% size distribution of the bone particles (µm–µm) | % by weight of particles in the composition formed hydrogel + bone particles | Ground fresh bones | γ-treated Bones particles |
|---|---|---|---|---|---|
| 68 | 500 | 400–600 | 10 | yes | |
| 69 | 500 | 400–600 | 50 | yes | |
| 70 | 500 | 400–600 | 25 | | yes |
| 71 | 1000 | 500–500 | 20 | yes | |
| 72 | 1000 | 500–1500 | 10 | yes | |
| 73 | 1000 | 500–1500 | 50 | | yes |
| 74 | 2000 | 500–2500 | 10 | yes | |
| 75 | 2000 | 1500–2500 | 20 | | yes |
| 76 | 2000 | 1500–2500 | 5 | yes | |

Examples 77 to 87

The hydrogel of example 1 has been prepared. After its preparation, the fibrin-fibrinogen hydrogel has been mixed with various materials. After said mixing, the hydrogel was lyophilized.

The following tables gives the material added and the amount of material added (expressed in % by weight of the composition hydrogel+added material).

| example | Material added | % by weight |
|---|---|---|
| 77 | collagen | 5 |
| 78 | collagen | 50 |
| 79 | Collagen | 25 |
| | Bone chips (average particle size 2000 µm) | 10 |
| 80 | fibronectin | 10 |
| 81 | fibronectin | 25 |
| 82 | Collagen | 10 |
| | fibronectin | 10 |
| 83 | Collagen (photo activable) | 30 |
| 84 | elastin | 15 |
| 85 | albumin | 10 |
| 86 | Recombinant collagen | 25 |
| 87 | Recombinant fibrin (photo activable) | 25 |

Examples 88 to 91

Example 1 has been repeated, except that the solution or hydrogel formed was sprayed in a chamber submitted to a low temperature (−20° C.) and a low pressure so as to produce a freeze drying of the sprayed particles. By adjusting the size of the sprayed particles, spherical particles having the structure of the invention were obtained.

The following table gives the average particle size of the spherical particles formed after lyophilization, as well as a particle size range corresponding to the particle size distribution at 90% (90% by weight of the particles formed after lyophilization having a size in the particle size range).

| Example | Average size (µm) | Range corresponding to the 90% distribution (µm–µm) |
|---|---|---|
| 88 | 500 | 400–600 |
| 89 | 750 | 700–800 |
| 90 | 1000 | 500–1500 |
| 91 | 2000 | 1500–2500 |

The so obtained particles can possibly be further dried if necessary and/or further treated.

Example 92

A kit consisting of a first container comprising a porous structure of the invention (for example in the form of a plate), said container keeping advantageously the structure under vacuum, and a second container containing an aqueous solution containing BMP, said solution being intended to be used for hydrating the porous structure of the first container.

The hydration of the porous structure is advantageously carried out just before use, for example within a period of I hour before its use.

Example 93

Example 1 has been repeated except that citric acid was added to the solution containing the fibrin-fibrinogen so that the polymerization is carried out at a pH of 4.5. After lyophilization, the lyophilised product was washed for removing the excess of citric acid.

Example 94

Example 1 has been repeated, except that the concentration of fibrinogen material and of the thrombin of the solution fibrinogen—thrombin—calcium blocking agent varied.

The diameter or thickness of the fiber of the cloth before lyophilization was estimated as equal to $$(44.1 \times K_S \times X^{1.3736})^{1/2}$$

with

X: (fibrinogen concentration g/ml)×6.62 ml/g (6.62 ml being the volume occupied by 1 g fibrinogen) and $K_S$=(Flux×length of the cloth×viscosity×$(10^{-2})$)/(P×A)
(Flux: ml/sec;
length: cm
P: dynes
A: the surface of the cloth=$\pi R^2$, R being the radius of the cloth
$K_S$ being expressed in $cm^2$)

| example | Fibrinogen Mg/ml | Thrombin IU/ml | KS cm² | Diameter μm |
|---|---|---|---|---|
| 94A | 25 | 4 | 6.9 10⁻¹² | 0.051 |
| 94B | 12.5 | 4 | 39.5 10⁻¹² | 0.075 |
| 94C | 25 | 250 | 8.9 10⁻¹² | 0.057 |
| 94D | 12.5 | 250 | 41 10⁻¹² | 0.077 |

From said table it appears that, when using the calcium blocking agent in an amount sufficient for blocking substantially all the calcium sites, the calculated diameter of the fiber of the cloth is substantially not dependent from the thrombin concentration, while when varying the fibrinogen concentration, it is possible to control the thickness or diameter of the fiber. The diameter decreases when decreasing the fibrinogen content of the solution.

However, the variation of diameter in function of the fibrinogen concentration is smooth, whereby enabling a good control of the desired fiber diameter in the cloth, whereby enabling to obtain after a lyophilization a product having specific and defined characteristics of wall thickness and porosity.

What I claim is:

1. Porous structure of fibrin or fibrinogen material, the structure comprising:

in its substantially dry form, a compression strain of less than 8%, and a creep modulus higher than $1.5 \times 10^6$ Pa, said compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute; and after hydration, such a porosity that at least 50% by volume of the total porosity is formed by channels with an open cross section of more than 500 $\mu m^2$.

2. The structure of claim 1, wherein the structure has after rehydration a compression strain of less than 8% and a creep modulus higher than $1.5 \times 10^6$ Pa, said compression strain and creep modulus being measured for a sample having a diameter of 5 mm on which a compression of 2500 milli Newtons is exerted with a compression ramp of 500 milli Newtons per minute, after a compression release step following an initial compression step of 2500 milli Newtons with a compression ramp of 500 milli Newtons per minute.

3. The structure of claim 1 further comprising a plurality of spaced walls defining cells therebetween, at least part of the cells are linked so as to define channels having after rehydration in cross section an open section greater than 500 $\mu m^2$.

4. The structure of claim 1 having a density calculated in its substantially dry form of less than about 0.5 g/cm³.

5. The structure of claim 3 wherein the walls have a mean thickness of less than about 100 μm.

6. The structure of claim 1 having a surface area of less than about 1 m²/g after the structure is rehydrated.

7. The structure of claim 1 further comprising calcium and phosphorous within an atomic ratio Ca/P from about 0.5 to about 5.

8. The structure of claim 1 further comprising calcium which is substantially not bound to albumin.

9. The structure of claim 1 being substantially free of albumin.

10. The structure of claim 1 is substantially pyrogen free.

11. The structure of claim 3 further comprising a binding agent on at least a part of the surface of the cells.

12. The structure of claim 1 further comprising an additive being selected from the group consisting of antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting the growth of endothelial cells on the fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_{12}$–$C_{24}$ fatty acids, collagen, and mixtures thereof.

13. The structure of claim 1, having a ratio of volume of the porous structure in its substantially dry form to the structure in its hydrated form of about 1.

14. The structure of claim 1 further comprising bone chips having a particle size of less than 2 mm.

15. The structure of claim 1 defining a powder having a grain size of less than about 1 mm.

16. A process for preparing a fibrin structure comprising the steps of:
  providing a solution containing at least about 5 mg/ml fibrin or fibrinogen;
  providing a calcium inhibiting agent;
  polymerizing the solution in the presence of the calcium inhibiting agent to cause at least partial cross-linking of the fibrin or fibrinogen materials to define a partially cross-linked fibrin or fibrinogen material;
  lyophilizing the partially cross-linked, fibrin or fibrinogen material to define a porous structure having the following physical characteristics:
    in its substantially dry form, a compression strain of less than 8% and a creep modulus higher than $1.5 \times 10^6$ Pa, the compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute, and
    after hydration, a porosity such that at least 50% by volume of the total porosity is formed by channels with an open cross section of more than 500 $\mu m^2$.

17. The process of claim 16, wherein the calcium inhibiting agent is present in an amount sufficient for reducing the cross-linking rate so as to obtain after the lyophilizing step a plurality of spaced walls defining therebetween channels, the channels having after rehydration in cross section an open section greater than 1000 $\mu m^2$.

18. The process of claim 16, wherein the calcium inhibiting agent is present in an amount sufficient for obtaining after the lyophilizing step a wall thickness of less than 100 $\mu m$.

19. The process of claim 16, wherein the calcium inhibiting agent is selected from the group consisting of: citrate salts, phosphate salts, oxalate salts and mixtures thereof.

20. The process of claim 16, wherein the polymerizing step includes an effective amount of the calcium inhibiting agent sufficient for increasing the clotting time to more than 30 seconds, said clotting time being measured at 37° C. in a stirred cuvette containing 0.5 ml of the fibrin or fibrinogen material.

21. The process of claim 16, wherein the lyophilizing step is carried out at a temperature of less than 40° C. and at a pressure of less than $0.4 \times 10^5$ Pa.

22. The process of claim 16 further including the step of adding a phosphate salt to the solution in an amount sufficient for having a Ca/P ratio from about 0.5 to about 5.

23. The process of claim 16 wherein the solution is substantially free of albumin.

24. The process of claim 16 further comprising the step of adding to the solution prior to, during or after the polymerizing step a compound selected from the group consisting of: antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, drugs, anti coagulants, poly DL lactate, alginate, recombinant material, triglycerides, fatty acids, $C_{12}$–$C_{24}$ fatty acids, and mixtures thereof or a solution containing at least one of said compound.

25. The process of claim 16 further comprising the step of after the lyophylizing step adding to the porous structure a compound selected from the group consisting of antibody, antimicrobial agent, agent for improving the biocompatibility of the structure, proteins, anticoagulants, anti-inflammatory compounds, compounds reducing graft rejection, living cells, cell growth inhibitors, agents stimulating endothelial cells, antibiotics, antiseptics, analgesics, antineoplastics, polypeptides, protease inhibitors, vitamins, cytokine, cytotoxins, minerals, interferons, hormones, polysaccharides, genetic materials, proteins promoting or stimulating the growth and/or attachment of endothelial cells on the cross-linked fibrin, growth factors, cell growth factors, growth factors for heparin bond, substances against cholesterol, pain killers, collagen, osteoblasts, chondroblasts, chondrocytes, osteoclasts, hematpoeitic cells, stromal cells, osteoprogenitor cells, anti coagulants, poly DL lactate, alginate, recombinant material, triglycerides, fatty acids, $C_{12}$–$C_{24}$ fatty acids, drugs, and mixtures thereof or a solution containing at least one of said compound.

26. The process of claim 16, wherein during the polymerizing step less than about 50% by weight of the fibrin or fibrinogen material is cross-linked.

27. The process of claim 16, wherein the calcium inhibiting agent is an antibiotic having anticoagulant property.

28. The process of claim 16, wherein the step of polymerizing is carried out at a pH from about 6 to about 10, and at a temperature from about 0° C. to about 60° C.

29. The process of claim 16, wherein the structure can be sterilized at a temperature below 0° C. by gamma radiation at a dosage of at least about 25 kGys.

30. The process of claim 16, wherein the porous material has an osmolarity greater than 175 mosm.

31. The process of claim 16, further comprising the step of spray-freeze drying the porous structure.

32. A kit for preparing a bone substitute, said kit comprising a first chamber containing an aqueous solution containing BMP and a second container containing a fibrin or fibrinogen material having the following physical characteristics:
  in its substantially dry form, a compression strain of less than 8%, and a creep modulus higher than 1.5 $10^6$ Pa, said compression strain and creep modulus being measured for a sample having a diameter of 5 mm on which a compression of 2500 milli Newtons is exerted with a compression ramp of 500 milli Newtons per minute, after a compression release step following an initial compression of 2500 milli Newtons with a compression ramp of 500 milli Newtons per minute; and
  after hydration, such a porosity that at least 50% by volume of the total porosity is formed by channels with an open cross section of more than 500 $\mu m^2$.

33. A cement for use with bones comprising:
  a solution containing a fibrin powder, and bone particles, the fibrin powder having the following physical characteristics:
    in its substantially dry form, a compression strain of less than 8%, and a creep modulus higher than $1.5 \times 10^6$ Pa, said compression strain and creep modulus being measured for a sample having a diameter of 5 mm on which a compression of 2500 milli New tons is exerted with a compression ramp of 500 milli Newtons per minute, after a compression release step following an initial compression of 2500 milli Newtons with a compression ramp of 500 milli Newtons per minute; and after hydration, such a porosity that at least 50% by volume of the total porosity is formed by channels with an open cross section of more than 500 $\mu m^2$.

* * * * *